United States Patent [19]

Tarsio et al.

[11] Patent Number: 4,797,473

[45] Date of Patent: Jan. 10, 1989

[54] MONOCLONAL ANTIBODIES TO UNREDUCED, NONENZYMATICALLY-GLYCATED PROTEINS

[75] Inventors: Joseph F. Tarsio; Leo T. Furcht, both of Minneapolis, Minn.

[73] Assignee: Regents of the University of Minnesota, Minneapolis, Minn.

[21] Appl. No.: 878,420

[22] Filed: Jun. 25, 1986

[51] Int. Cl.[4] .................. C07K 15/04; A61K 39/395; C12N 5/00; G01N 33/577
[52] U.S. Cl. ........................................ 530/387; 435/7; 435/68; 435/172.2; 435/240.27; 435/100; 435/104; 435/110; 436/548; 424/85.0; 424/88
[58] Field of Search ............. 435/7, 68, 70, 172.2, 435/240, 241, 948, 240.27; 530/387, 388, 809, 380, 395, 808; 436/536, 540, 542, 548, 815, 819, 67, 87; 935/99, 100, 102, 103, 104, 110; 424/85, 88

[56] References Cited

U.S. PATENT DOCUMENTS

| | | |
|---|---|---|
| 4,247,533 | 1/1981 | Cerami et al. ................. 424/1 |
| 4,478,744 | 10/1984 | Mezei ......................... 424/88 |
| 4,629,692 | 12/1986 | Dean .......................... 435/7 |
| 4,647,654 | 3/1987 | Knowles ..................... 530/326 |
| 4,658,022 | 4/1987 | Knowles ..................... 530/402 |

OTHER PUBLICATIONS

Tsang; V. C. W. et al., Methods in Enzymology, vol. 92, pp. 391–403 (1983).
J. Javid et al., Brit. J. Haematology, 38, 329 (1978).
L. K. Curtiss et al., J. Clin. Invest., 72, 1427 (10–1983).
J. F. Tarsio et al., Diabetes, 34, 477 (1985).
S. L. Palm et al., J. Cell Biology, 96, 1218 (1983).

Primary Examiner—Margaret Moskowitz
Attorney, Agent, or Firm—Merchant, Gould, Smith, Edell, Welter & Schmidt

[57] ABSTRACT

A hybridoma is provided which yields a monoclonal antibody which binds to an epitope on an unreduced, nonenzymatically-glycated plasma protein, and which is substantially free of cross-reactivity with the corresponding non-glycated plasma protein.

22 Claims, No Drawings

MONOCLONAL ANTIBODIES TO UNREDUCED, NONENZYMATICALLY-GLYCATED PROTEINS

The present invention was made with the assistance of Grant No. AM 32660 from The National Institutes of Health. The Government has certain rights in the invention.

BACKGROUND OF THE INVENTION

A key biochemical change observed in diabetes mellitus in humans and in animal models of the disease is an increase in the chemcial attachment of glucose to proteins which occurs without the aid of enzymes ("nonenzymatic glycation," formerly called "nonenzymatic glycosylation"). This occurs due to the increased glucose concentration in the blood of poorly-controlled diabetics. Therefore, the amount of nonenzymatic glycation of a given protein is indicative of how well a diabetic is controlling his or her blood glucose concentration, and may also be of value in predicting the progression of tissue complications that occur in diabetes such as renal, ocular, microvaascular and nervous system disease.

Many proteins such as hemoglobin, albunim, fibrinogen, fibrin, low density lipoproteins (LDL), lens crystallins, peripheral nerve proteins, interstitial collagens and type IV basement membrane collagen, have been found to be nonenzymatically glycated to a greater extent in diabetic patients than in normal subjects. The glycation reaction results in the attachment of glucose to proteins via nucleophilic addition to form a Schiff base between glucose and the N-terminal amino group of apolypeptide or the epsilon-amino group of a lysine residue in the polypeptide chain. The formation of the initial linkage (the labile glucose adduct formed via an aldimine linkage) is reversible. Therefore, the Schiff base reaches an equilibrium level in vivo which reflects the ambient glucose concentrations. With time, however, there is a slow chemical rearrangement of the Schiff base (termed an Amadori rearrangement") which results in the formation of a stable ketoamine (the 1-amino-1-deoxy-2-keto adduct termed the Amadori product"). The kinetics of these reactions have been documented by studies of the steps involved in the formation of the glycated Amadori product, hemoglobin A1c.

In terms of the tissue complications of diabetes mellitus, the nonenzymatic glycation of various proteins has been implicated in a number of pathological sequelae, including the progression of kidney disease, cataract formation, neuropathy, and atherosclerosis. For example, glycation of hemoglobin alters its affinity for oxygen. Lens crystallin glycation results in opacification and may contribute to cataract formation. Glycation of collagen alters the extent and perhaps the type of collagen cross-linking that leads to stiffening of tissues. Glycation of LDL alters cellular uptake and degradation of this protein. The nonenzymatic glycation of fibronectin, laminin and type IV collagen alters the molecular association of these molecules with each other and with heparan sulfate proteoglycan, and may alter the composition of basement membranes in tissues affected by the complications of diabetes.

The development of quantitative methods for the measurement of the nonenzymatic glycation of proteins has been carried out mainly on hemoglobin. Because of the relatively long half-life of red blood cells (approximately 60 days), when properly done, the glycosylated hemoglobin assay provides a retrospective index of glucose control in patients that correlates well with mean plasma glucose levels, 24-hour urinary glucose concentrations, and other indexes of metabolic control determined over the preceding two to three months.

However, the quantitation of glycation levels in proteins other than hemoglobin is important since other readily accessible proteins in plasma, urine, or tissue biopsies can provide information about glycemic control within different time frames. For example, the half-life of albumin or low density lipoproteins is 3 to 5 days and the measurement of the glycation of these proteins may indicate the degree of glucose control over a very short period of time. On the other hand, the quantitation of glycation levels of skin collagen (half-life of approximately 2–3 years), for example, would indicate the ability of diabetic subjects to regulate glucose concentrations over a much longer period of time than that which can be determined by measuring glycated hemoglobin.

Assays have been designed to measure the total glycation levels of the adult form of hemoglobin (hemoglobin A). This glycated fraction of hemoglobin A (termed "hemoglobin $A_1$" is modified by glucose at $\beta$-chain terminal valine residues and at epsilon-amine groups of internal lysine residues and is more negatively charged than normal hemoglobin A (unmodified hemoglobin or hemoglobin A0). Hemoglobin A1c, another clinically useful substrate for the measurement of nonenzymatic glycation, on the other hand, is a subfraction of hemoglobin A1 which consists of hemoglobin A glycated by a ketoamine linkage at only the $\beta$-chain terminal valine residue.

Immunological approaches to the measurement of the levels of nonenzymatic glycation of hemoglobin have been attempted using $^{125}$I-labelled antibody in a radioimmunoassay. The first of these approaches is based on the observation that glycated products cannot be demonstrated in sheep red cell hemolysates. This may be because sheep hemoglobin lacks the "diphosphoglycerate pocket" which permits the glycation of the $\beta$-chain N-terminus of hemoglobin. The sheep, as disclosed by J. Javid, et al., *Brit. J. Haematology*, 38, 329 (1978), therefore, recognizes the N-terminus of human hemoglobin A1c as foreign and produces an antibody against it. However, this polyclonal antibody is difficult to raise and it also cross-reacts with hemoglobin A1a and hemoglobin A1b, chromatographically-stable components of hemoglobin A1 which are distinct from the A1c species. The A1c antisera must also be repeatedly absorbed with agarose-linked hemoglobin A0 at the expense of a considerable loss of antibody titer. The observation that the antibody to human A1c reacts less well with dog and mouse hemoglobin A1c also raises the possibility that the steric fit of the antibody includes more than the sugar molecule and probably extends to surface features of the protein adjacent to the glucose modification.

L.K. Curtiss, et al., in *J. Clin. Invest.*, 72, 1427 (1983) have disclosed the formation of murine monoclonal antibodies which react with nonenzymatically-glycated murine low density lipoprotein. However, the glucose adducts on the protein had to be first chemically reduced with sodium borohydride or sodium cyanoborohydride to yield an immunogenic hexose alcohol (glucitol-lysine) since these authors did not succeed in raising monoclonal antibodies to the unreduced adducts naturally found on proteins in diabetic tissues (the labile Schiff's base or Amadori product). It would, therefore, also be necessary to reduce the target proteins in a test sample in a similar fashion to produce glucitol-lysine residues in order to obtain reaction with the antibody. The clinical utility of this method remains to be determined, especially since the detection of various glycated epsilon-amino groups of lysine on a protein is limited to those that can be selectively reduced by chemical-reducing agents in vitro.

Therefore, a need exists for monoclonal antibodies which recognize and will selectively react with the unmodified Schiff's base or Amadori glucose adducts which result from the nonenzymatic glycation of proteins, such as the proteins associated with physiological fluids such as blood and lymph.

BRIEF DESCRIPTION OF THE INVENTION

The present invention provides a monoclonal antibody (MCA) which binds to an epitope on an unreduced, nonenzymatically-glycated plasma protein, and which is substantially free of cross-reactivity with the corresponding non-glycated plasma protein. The present invention is also directed to a hybridoma produced by a process comprising:

(a) immunizing mammalian B lymphocytes with an unreduced, nonenzymatically-glycated plasma protein;
(b) recovering the immunized B lymphocytes;
(c) fusing said recovered B lymphocytes with malignant mammalian B lymphocytes to produce hybridomas;
(d) selecting from said hybridomas a hybridoma which produces a monoclonal antibody which binds to an epitope on an unreduced, nonenzymatically-glycated plasma protein, and which is substantially free of cross-reactivity with the corresponding non-glycated plasma protein; and
(e) clonally expanding said selected hybridoma.

In accordance with one embodiment of the present invention, a mouse or other mammal is immunized with an imunogen comprising an unreduced, nonenzymatically-glycated murine blood plasma protein, and the B lymphocytes are recovered from the spleen of the immunized mammal. These lymphocytes can be fused with murine myeloma cells to yield hybridomas. The hybridomas or the surrounding growth media can be tested for the presence of the desired MCA, e.g., one which exhibits differential reaction between the unreduced, nonenzymatically-glycated plasma protein employed for the immunization and the corresponding non-glycated plasma protein. The preferred hybridomas secrete MCAa which exhibit the ability to differentiate between the unglycated and the unreduced, nonenzymatically-glycated forms of a human serum or plasma proteins such as transferrin, albumin, fibronectin and the like.

Therefore, in accord with the present invention, monoclonal antibodies have been provided which exhibit differential reactivity between unreduced, nonenzymatically-glycated plasma proteins and the corresponding non-glycated plasma proteins, to the extent that they are substantially free of cross-reactivity with non-glycated plasma proteins. For example, in the enzyme-linked immunosorbent assay (ELISA) used for the differential screening of monoclonal antibodies produced by the present hybridomas above, monoclonal antibodies which yielded at least a 35%, and preferably at least a 75%, increase in absorbance units (A) when reacted with an unglycted, normal protein can exhibit useful differential recognition with respect to these protein species.

Furthermore, the present MCAs may bind selectively to the unreduced, glycated member of a second glycated/nonglycated protein pair, and this binding may be more selective than the binding to the first glycated protein employed in the immunization step (a), over the corresponding non-glycated first protein. For example, an MCA produced by immunization with a murine glycated protein may exhibit a greater degree of selectivity with respect to its binding to a human glycated protein.

As used herein with respect to plasma or serum proteins, the term "unreduced" is intended to mean that the Schiff base or the correesponding ketoamine product thereof which is formed when plasma proteins are monenzymatically-glycated in vitro or in vivo is not subjected to a further in vitro chemical reduction, e.g., to increase the stability of the glucose-protein bond. Therefore, the present hybrodimas produce antibodies which can recognize epitopes associated with the initial glucose modification of the plasma protein. In contrast to the disclosure of L.K. Curtiss, et al., supra, reduction of the "natural" glucose-protein adducts to the sugar-alcohol form (glucitol-lysine) is not necessary for antibody generation or for the measurement of nonenzymatic protein glycation. Therefore, the qualitative or quantitative level of reduction of the immunogenic protein produced in vitro is not a factor in the production of the present hybridomas or in the specificity of the monoclonal antibodies produced thereby.

Finally, the extent of the binding of the MCAs of the present invention to a given unreduced, nonenzymatically-glycated protein will increase in proportion to the number of glycated sites on the target protein. This property facilitates the ability of the MCAs to detect the extent as well as the presence of plasma protein glycation.

Although the present monoclonal antibodies are characterized primarily in terms of their ability to react with nonenzymatically-glycated proteins which are present in blood serum or plasma, it is expected that these monoclonal antibodies will exhibit the ability to selectively bind to nonenzymatically-glycated proteins present in tissues or other physiological fluids such as saliva, lymph, urine, sperm, ocular fluids and the like. Therefore, the present invention is also directed to a method for detecting the presence of an unreduced, nonenzymatically-glycated protein in a sample of a tissue or a physiological fluid, such as a sample of blood or urine, which comprises reacting said sample with a monoclonal antibody of the present invention which binds to an epitope on said unreduced, nonenzymatically-glycated protein, said MCA being substantially free of cross-reactivity with the corresponding non-glycated serum protein. The presence of the MCA-protein complex can be determined by an assay comprising reacting the MCA-protein complex with a second antibody which is bound to a detectable label, which antibody binds to a site on the MCA. The details of an enzyme-linked immunosorbent assay which employs a second antibody which is enzyme-labelled are fully presented hereinbelow.

DETAILED DESCRIPTION OF THE INVENTION

Monoclonal Antibodies

The general techniques for producing monoclonal antibodies are based on the fusion of immunized mammalian B lymphocytes with malignant mammalian B lymphocytes. For example, spleen lymphocytes can be fused with malignant cells (myelomas) of bone marrow primary tumors [C. Milstein, *Sci. Am.*, 243, 66 (1980)]. The methods yield fused cell hybrids, or hybridomas, which can be clonally expanded to yield a series of hybrid cell lines, each of which is derived from a single hybridoma, or clone.

Each hybridoma possesses characteristics of both the lymphocytes and myeloma primed with sheep red blood cells as antigens, the hybridomas secrete antibodies (immunoglobulins) reactive with the antigen. Moreover, like the myeloma cell lines, the hybridomas are immortal. Specifically, whereas antisera derived from vaccinated animals are variable mixtures of antibodies which cannot be identically reproduced, the single type of immunoglobulin secreted by a hybridoma is specific to one and only one antigenic determinant on the antigen, a complex molecule having a multiplicity of antigenic molecular substructures, or determinants (epitopes). For instance, if the antigen is a glycated protein, the epitope may be one of the many molecular substructures associated with the glucose-amino acid bonds. Hence, monoclonal antibodies raised against a single antigen may be distinct from each other depending on the determinant that induced their formation. However, all of the antibodies produced by a given clone are identical. Furthermore, preferred hybridoma cell lines can be reproduced indefinitely, are easily propagated in vitro or in vivo, and can yield monoclonal antibodies in extremely high concentrations.

1. Antigens

In accord with the present invention, the antigens which can be used to immunize the B lymphocyteproducer mammal can be selected from a wide variety of unreduced, nonenzymatically-glycated blood plasma proteins. Such proteins include laminin, albumin, immunoglobulin, transferrin, low-density lipoproteins, fibrinogen, fibronectin, plasminogen, plasmin and mixtures thereof. For example, unreduced, nonenzymatically-glycated total serum proteins can be used as the antigenic preparation.

General methods for the production of nonenzymatically-glycated proteins from various proteins have been developed, i.e., by J.F. Tarsio, et al., *Diabetes*, 34, 477 (1985), the disclosure of which is incorporated by reference herein. In a typical procedure, a mixture of the protein or proteins in a buffered physiological salt solution such as phosphate-buffered saline (PBS) is incubated with D-glucose for 10-20 days under ambient conditions, preferably in the present of an effective amount of protease inhibitors and preservatives. The glycated protein can be isolated by dialysis, resuspended in a physiological salt solution for the desired concentration, and an effective amount thereof employed to immunize the mammal. Preferably, the number of mammalian B-cells producing antibodies reactive with the immunogen is increased by additional immunizations ("boosting"). Methods are also available for the in vitro immunization of mammalian lymphocytes.

Although unreduced, nonenzymatically-glycated murine serum proteins are convenient immunogens for use in the present invention, other unreduced, glycated mammalian proteins, such as those derived from humans, sheep, goats, rabbits and the like, may also be employed. Naturally-derived or chemically-synthesized immunogenic fragments of such proteins can be also employed in the immunization protocol, and such fragments are intended to be encompassed within the term "unreduced nonenzymatically-glycated plasma protein".

2. Somatic Cells

Somatic cells with the potential for producing antibody, and in particular B lymphocytes, are suitable for fusion with a B-cell myeloma line. Those antibody-producing cells undergoing mitosis fuse preferentially. Lymph nodes and spleens of the primed animals are convenient lymphatic organs for use in the present fusion system. Once-primed or hyperimmunized animals can be used as a source of antibody-producing lymphocytes. Mouse and rat lymphocytes give a higher percentage of stable fusions with the mouse myeloma lines described below. However, the use of rabbit, human, primate and frog cells is also possible. In the preferred embodiments, hyperimmunized mouse spleen cells are used to make the fused cell hybrids, or hybridomas.

3. Myeloma Cells

Specialized myeloma cell lines have been developed from lymphocyte tumors for use in hybridoma-producing fusion procedures [G. Kohler and C. Milstein, *Eur. J. Immunol.*, 6, 511 (1976); M. Shulman, et al., *Nature*, 276, 269 (1978)]. The cell lines have been developed to facilitate the selection of fused hybridomas among unfused and similarly indefinitely self-propagating myeloma cells by using myelomas with enzyme deficiencies that render tham incapable of growing in certain selective media that support the growth of hybridomas. Furthermore, myeloma cell lines incapable of producing light or heavy immunoglobulin chains or those deficient in antibody secretion mechanisms can be used. A third reason for selection of cell lines is for their suitability and efficiency for fusion.

Several myeloma cell lines may be used for the production of fused cell hybrids, including P3/X63-AG 8.653, Pc/NSI/1-Ag 4.1 ("NS-1"), Sp2/O-Ag14 and S194/5.XXO.BU.1. The P3/X63-Ag 8 and P3/NSI/1-Ag 4.1 cell lines have been described by Kohler and Milstein [*Eur. J. Immunol.*, 6, 511 (1976)] and by J. Kearney, et al., *J. Immunol.*, 123, 1548 (1979). Shulman, et al., *Nature*, 276, 269 (1978), developed the Sp2/O-Ag14 myeloma line. The S194/5.XXO.BU.1 myeloma line was reported in an article by Trowbridge [*J. Exp. Med.*, 148, 313 (1979)].

4. Fusion

Methods for generating hybrids of antibody-producing spleen or lymph node cells and myeloma cells usually comprise mixing somatic cells with myeloma cells in the presence of an agent or agents that promote the fusion of cell membranes. It is preferred that the same species of animal serve as the source of the somatic and myeloma cells used in the fusion procedure. Fusion methods have been described by Kohler and Milstein in *Nature*, 256, 495 (1975) and *Eur. J. Immunol.*, 6, 511 (1976), and by Gefter, et al., in *Somatic Cell Genet.*, 3, 231 (1977). The fusion-promoting agents used by those investigators were Sendai virus and polyethylene glycol (PEG), respectively.

5. Isolation of Clones and Antibody Detection and Production

Generally, the selection of fused cell hybrids is accomplished by culturing the cells in media that support the growth of hybridomas but prevent the growth of the unfused myeloma cells which normally would go on dividing indefinitely. In the example of the present invention, myeloma cells lacking hypoxanthine phosphoribosyl transferase (HPRT−) were used. These cells are selected against in hypoxanthine/aminopterin/thymidine (HAT) medium, a medium in which the fused cell hybrids survive due to the HPRT-positive phenotype of the spleen cells. The use of myeloma cells with different genetic deficiencies (e.g., other enzyme deficiencies, drug sensitivities, and the like) that can be selected against in media supporting the growth of genotypically-competent hybrids is also possible.

Several weeks can be required to selectively culture the fused cell hybrids. Early in this time period, it is necessary to identify those hybridomas which produce the desired antibody so that they may be subsequently cloned and propagated. The detection of antibody-producing hybrids can be achieved by any one of the several standard assay methods, including indirect imunofluorescence, enzyme-linked immunosorbent assay and radioimunoassay techniques which have been described in the literature [R. Kennet, T. McKearn and K. Bechtol (editors), *Monoclonal Antibodies, Hybridomas; a New Dimension in Biological Analysis,* Plenum Press, New York (1980) at pages 376–384].

Once the desired fused cell hybrids have been selected and cloned into individual antibody-producing cell lines, each cell line may be propagated in either of two standard ways. A sample of the hybridoma can be injected into a histocompatible animal of the type that was used to provide the somatic and myeloma cells for the original fusion. The injected animal develops a malignant ascites or bulky tumors secreting the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium, also containing high concentrations of a single specific monoclonal antibody, can be harvested by decantation, filtration or centrifugation, and the antibody isolated therefrom.

6. Characterization of Monoclonal Antibodies

The binding specificity of the present monoclonal antibodies with respect to glycated proteins can also be determined by means of a differential enzyme-linked immunosorbent assay. In this assay, a known amount of the glycated protein or the control non-glycated protein is physically immobilized in the wells of a test plate and contacted with an excess of the monoclonal antibody, e.g., by the addition of a portion of spent culture medium from a given hybridoma. After a suitable incubation period, the protein-MCA complex is washed to free it of unbound MCA and the bound MCA is detected with a commercially-available anti-mouse antibody which is bound to a detectable label such as fluorescein isothiocyanate or a peroxidase. The presence of the peroxidase congugate can be measured colorimetrically as absorbance units by contacting it with a developer such as o-phenylenediamine. The difference, if any, in the absorbance values (A) observed for the glycated protein versus the non-glycated control protein provides a comparative measure of the ability of a given MCA to bind to an epitope associated with a glycation site.

The differential ELISA can also be employed to detect the extend of glycation of a protein or proteins present in a physiological fluid of a mammal which is known or suspected to be diabetic. For example, a sample of the fluid drawn from the mammal, such as blood serum, can be immobilized, as in the wells of the test plate, and the extent of its binding to an MCA of the present invention can be determined relative to an immobilized sample of fluid from a non-diabetic control mammal. The relative extent of the glycation of the target protein can then be empirically correlatd to the extent of the related tissue pathology.

The invention will be further described by reference in the following detailed examples.

EXAMPLE I

Preparation of Glycated Protein Antigens

Mouse nonenzymatically-glycated proteins were produced and used as antigens to stimulate antibody production in Balb/c mice. Two separate murine-protein preparations were utilized to immunize mice--nonenzymatically-glycated laminin and nonenzymatically-glycated total serum proteins.

Laminin, an extracellular matrix protein of 850,000 molecular weight, was first purified from the mouse EHS tumor by the method of S. L. Palm, et al., in *J. Cell Biol.,* 96, 1218 (1983). Purified laminin (25 mg) at 1 mg/ml was then incubated for 12 days at 37° C. with 500 mM D-glucose in phosphate buffered saline (PBS, pH 7.4) containing 1 mM sodium azide as a preservative. The protein was protected from proteolytic degradation over this long period of in vitro incubation by the addition of protease inhibitors to give a final concentration of 372.2 mg/L disodium ethylenediamine tetracetate (Na2EDTA), 34.8 mg/L phenylmethylsufonyl fluoride (PMSF), 0.7 mg/L pepstatin A, 0.5 mg/L leupeptin, and 4.5 trypsin inhibitory units of aprotinin/ml (all from Sigma Chemical Co., St. Louis, MS). After 12 days of incubation, unreactive sugars, azide, and protease inhibitors wree removed by dialysis against six changes of 2L of PBS buffer.

The second antigen preparation consisted of mouse-glycated total serum proteins. It was prepared by obtaining blood by heart puncture from 9 Balb/c mice (16 weeks old, male or female), allowing it to clot for 30 minutes at room temperature (with moderate hemolysis), and collecting the serum. The serum was then incubated in vitro with 500 mM D-glucose and protease inhibitors and dialyzed as described hereinabove to yield nonenzymatically-glycated total serum proteins.

EXAMPLE II

Production and Evaluation of Hybridomas

A. Immunization

Nonenzymatically-glycated laminin (25 μg) was suspended in 0.1 ml of PBS buffer and mixed with 0.1 ml of complete Freund's adjuvant and injected intraperitonealy (i.p.) into each of five female Balb/c mice (8 weeks old). Nonenzymatically-glycated total serum proteins were suspended in PBS and prepared for administration as for nonenzymatically-glycated laminin and injected i.p. into 5 other mice as described above for laminin. On days 22 and 76, secondary injections of 20 μg of nonenzymatically-glycated laminin (gLMN) were given i.p. in incomplete Freund's adjuvant to the mice that received the initial injection of nonenzymatically-glycated laminin. Likewise, 25 μg of nonenzymatically-glycated total serum proteins (gTSP) were given i.p. at these times in incomplete Freund's adjuvant to the mice that had received the initial gTSP injection. Three days before fusion, (day 83), the mice were given i.p. injections of 25 μg of gLMN or gTSP as described above for secondary immunization.

B. Hybridomas

Hybridomas were made by two separate fusions. One fusion was performed by incubating spleen cells from a gLMN-immunized mouse with P3/NSI/1-Ag 4.1 mouse myeloma cells and the other fusion consisted of mixing spleen cells from a gTSP-immunized mouse with P3/NSI/1-Ag 4.1 cells. Fusions were done in the presence of 35% (wt/v) of polyethylene glycol-1000 at ratio of 10 spleen cells/myeloma cell (one spleen yields $1 \times 10^8$ cells and is mixed with $1 \times 10^7$ NS-1 myeloma cells) as described by G. Galfre, et al., *Nature*, 266, 550 (1977), the disclosure of which is incorporated by reference herein. Cell preparations were then plated out (at $2 \times 10^6$ cells per well) in 24 well tissue culture plates in 1 ml of standard HAT medium (Dulbecco's Minimal Essential Medium containing 12 mM hypoxanthine, 9 μM aminopterine and 8 mM thymidine) containing 20% (v/v) horse serum. This yielded 72 wells with the gLMN-immunized spleen×NS-1 myeloma cells (designated fusions 1 through 72) and 72 wells with the gTSP-immunized spleen×NS-1 cells (designated fusions 73 through 144).

After three days, 50% of the medium in each well was removed, discarded and replaced with the same amount of fresh HAT medium containing 20% horse serum. The cells were then fed in this manner on days 6, 9 and 12 after fusion and the spent medium that was removed on day 12 was kept frozen (at $-10°$ C.) for screening for specific antibody production (as described hereinbelow). On and after day 14 from the initial fusion, the cells from the fusions that showed the best growth and were positive in the differential screening procedure described hereinbelow were clonally expanded. The cells were plated into a 96 well microtiter plate at a concentration of 1 cell/well in 0.2 ml of HAT medium containing 20% serum and 10% (v/v) normal spleen cell-conditioned medium [G. Galfre, et al., *Methods Enzymol.*, 73, 1-46 (1981)]. Growth was followed microscopically over the next three weeks, and wells were selected for screening for specific antibody production that showed one clone per well. Each clone was designated by the original fusion number (i.e., 1-144) followed by a dash and the letter and number designation of the well in the microtiter plate in which the clone was produced. For example, 10-C10 would designate the 10th fusion well (also indicating that gLMN was the antigen) that produced a clonal cell line in well C0 of the microtiter plate. As a further example, 83-D10 would designate the 83rd original fusion well (also indicating that gTSP was the antigen) and the location of the clone in this microtiter plate (D10).

C. Differential Screening Procedure

Selection of the clones that would be further expanded was based on the results of a differential enzyme-linked immunosorbent screening procedure that detects a clone that shows a good antibody reaction to its nonenzymatically-glycated immunogen (gLMN or gTSP) but not to protein preparations that have not been nonenzymatically-glycated in vitro (cLMN or cTSP designating control laminin and control total serum proteins respectively). The unglycated control proteins were treated as above for the nonenzymatically-glycated proteins except that no glucose was added to the incubation mixture.

For the ELISA assays, 5 μg of each antigen or its respective control protein were made up of 1 ml of PBS buffer and 0.1 ml was added to each well of a 96 well polystrene microtiter plate. Plates were covered with pressure sensitive film and incubated overnight at 37° C. Plates were then stored at 4° C. until ready to use.

Prior to use, the plates were washed 5 times using a Nunc Immune Wash 12 with PBS-Tween [made by mixing 200 ml of 10×PBS with 42.4 g NaCl, bringing the volume to 2 L with distilled water, adding 10 ml of polyoxethylene sorbitan monolaurate (Tween 20) and adjusting the pH to 8.0]. Any PBS-Tween remaining in the wells were blotted dry from the plate onto absorbent paper towels.

Spent medium (100 μl) that was removed from a given cloned cell was then added to each well containing the immobilized gLMN antigen or the cLMN protein for each clone derived from fusions 1 through 72. Likewise, 100 μl of spent medium from each clone from fusions 73 through 144 were added to each well containing immobilized g TSP or cTSP. The plates were then incubated for 2 hr at 37° C. with moderate shaking on a circular paltform shaker. After 2 hr, the plates were washed 5 times as described above with PBS-Tween. Peroxidase-conjugated goat anti-mouse immoglobulins (IgA, IgG and IgM, heavy and light chain specific) (Cooper Biomedical, West Chester, PA) (100 μl) diluted to 1:500 in PBS-Tween were then added to the wells of the microtiter plate. The plates were then incubated for 2 hr at 37° C. as described hereinabove. After 2 hr of incubation with the labelled antibody, the plates were washed 5 times with PBS-Tween and 100 μl of substrate solution were added to each well (substrate solution consisted of 50 μl of 30% hydrogen peroxide and 20 mg ortho phenylenediamine in 50 ml of PBS-Tween). About 5-10 minutes after the addition of substrate solution, the solution in the positive wells began to turn brown. After 10-15 minutes (before the wells turn very brown), 50 μl of 2.5 M $H_2SO_4$ was added to each well to stop the color developing reaction. Plates were then read with a Micro Elisa Reader at 490 nm. The Reader was adjusted as close as possible to zero using control wells that contained conditioned medium from an unrelated hybridoma clone (not produced to glycated proteins or their normal counterparts). Therefore, IgA, IgG or IgM secreting hybridoma clones that strongly recognized glycated antigens were detected in this assay by a high absorbance reading (approximately 25 to 150% greater with the glycated antigens gLMN or gTSP then the respective control antigens cLMN or cTSP).

D. Results

Of the 144 fusion wells plated, 21 fusion products initially yielded hybridomas which grew well and gave positive results when assayed by the differential screening procedure described hereinabove (13 for the gLMN antigen and 8 for the gTSP antigen). Eleven of these 21 fusion products continued to grow well, did not show microbial contamination and were selected for cloning (numbers 2, 10, 26 and 49 from the gLMN fusion and numbers 74, 80, 83, 84, 88, 89 and 00 from the gTSP fusions). Several fusion wells did not produce clones (numbers 2, 49, 88 and 100). The number of clones obtained per 96 wells for each of the remaining fusions varied (ranging from a total of 3 clones for fusion no. 26 to a total of 29 clones for fusion no. 84). When clones that continued to show good growth were screened by the differential screening procedure described above, a total of 4 positive hybridomas for the gLMN fusions (Table I) and 19 positive hybridomas for the gTSP fusions (see Table II) were detected.

TABLE I

Differential Screening of Spent Medium from Cloned Hybridomas Against Laminin Antigens

| Hybridoma | $A_{490}$ of cLMN | $A_{490}$ of gLMN | % change from control |
|---|---|---|---|
| 10-H9 | 0.71 | 1.33 | 87.3 |
| 26-B5 | 0.83 | 1.19 | 43.4 |
| 10-C10 | 0.26 | 0.37 | 42.3 |
| 26-G10 | 0.84 | 1.18 | 40.5 |

TABLE II

Differential Screening of Spent Medium from Cloned Hybridomas against Total Serum Protein Antigens

| Hybridoma | $A_{490}$ of cTSP | $A_{490}$ of gTSP | % change from control |
|---|---|---|---|
| 74-G11 | 0.20 | 0.49 | 145.0 |
| 83-D10 | 0.33 | 0.64 | 93.9 |
| 84-F6 | 0.67 | 1.21 | 80.6 |
| 79-H3 | 0.35 | 0.60 | 71.4 |
| 74-D10 | 0.45 | 0.76 | 68.9 |
| 80-H3 | 0.34 | 0.64 | 64.1 |
| 84-C11 | 1.09 | 1.77 | 62.4 |
| 74-F3 | 0.48 | 0.77 | 60.4 |
| 80-E11 | 0.66 | 1.01 | 53.0 |
| 89-G4 | 0.81 | 1.22 | 50.6 |
| 84-G9 | 0.90 | 1.34 | 48.9 |
| 84-F12 | 0.95 | 1.41 | 48.4 |
| 84-H5 | 0.86 | 1.27 | 47.7 |
| 84-G1 | 1.09 | 1.60 | 46.8 |
| 84-F9 | 1.14 | 1.67 | 46.5 |
| 84-H3 | 0.78 | 1.10 | 41.0 |
| 84-F3 | 1.15 | 1.57 | 36.5 |
| 84-H9 | 0.90 | 1.16 | 28.9 |
| 89-G10 | 1.10 | 1.31 | 26.0 |

Spent medium from the hybridomas listed in Tables I and II were tested against plasma from diabetic and normal rats using the ELISA assay described above. The test antigens in the assay were plasma from either of two diabetic rats (sample no. 1 or sample no. 2).

Male Lewis rats, weighing 100–125 g. matched for age, were purchased from Simonsen Laboratories (Gilroy, GA) and made diabetic following an 18-hour fast by injection of streptozotocin (Upjohn Co., Kalamazoo, MI). Streptozotocin was made up in citric acid buffer, pH 4.5, to 1.3 gram% solution and a dosage of 65 mg of streptozotocin/kg weight of the animal was administered intravenously by tail vein injection. This was followed by intraperitoneal injection of 2 ml of a 30% (w/v) solution of glucose in saline. Control animals were treated as above except that they wer egiven an intravenous injection of citric acid buffer containing no streptozotocin. Using this protocol, Steffes, et a., in Diabetes, 29, 509 (1980), have shown poor control of glucose and discernable diabetic lesions such as increased glomerular basement membrane width and increased glomerular and mesangial volumes 6-9 months after the injection of streptozotocin.

Each plasma sample was taken 22 months after the administration of streptozotocin. The control sample was plasma from a control rat (taken 22 months after the injection of citrate buffer). The absorbances at 490 nm obtained in the ELISA assay for the binding of monoclonal antibody from a given hybridoma to the controlor diabetic plasma samples are given in Table III along with the percent change in absorbance from the control obtained for each of the diabetic samples. The media from six hybridomas contained monoclonal antibodies which resulted in a significant increase in absorbance for the diabetic samples above that of the control.

TABLE III

Differential Screening of Spent Medium from Clonal Cell Lines Against Adult Rat Plasma

| Medium from Hybridoma | $A_{490}$ with control rat plasma | $A_{490}$ with diabetic rat plasma (Sample No. 1) | $A_{490}$ with diabetic rat plasma (Sample No. 2) | % change from control: Sample no. 1 | % change from control: Sample no. 2 |
|---|---|---|---|---|---|
| 26-B5 | 0.31 | 0.62 | 0.63 | 100.0 | 103.2 |
| 83-D10 | 0.32 | 0.55 | 0.64 | 71.9 | 100.0 |
| 84-F9 | 0.37 | 0.52 | 0.58 | 40.5 | 56.8 |
| 10-C10 | 0.32 | 0.42 | 0.44 | 31.3 | 37.5 |
| 79-H3 | 0.32 | 0.39 | 0.39 | 21.9 | 21.9 |
| 10-H9 | 0.40 | 0.45 | 0.48 | 12.5 | 20.0 |

Spent medium from the hybridomas in Tables I and II were also tested for the ability of antibodies from each cell line to recognize nonenzymatically-glycated human plasma fibronectin using the ELISA assay. The increase in absorbance in the ELISA assay when the spent medium from a given hybridoma was tested against nonenzymatically-glycated fibronectin as antigen above the absorbance which was found when the medium was tested against fibronectin that was not glycated in vitro was evaluated.

Twelve-day nonenzymatically-glycated human fibronectin and its normal counterpart were prepared by the incubation of 25 mg of the protein (at 1 mg/ml) at 37° C. with 500 mM D-glucose in phosphate-buffered saline (PBS, pH 7.4) containing 1 mM sodium azide as a preservative. Protease inhibitors were also added to the incubation buffer to give a final concentration of 372.2 mg/L disodium theylenediamine tetraacetate (Na2-EDTA), 34.8 mg/L phenylmethylsulfonyl flouride (PMSF), 0.7 mg/L pepstatin A, 0.5 mg/L leupeptin, and 4.5 trypsin inhibitor units of aprotinin/ml (all from Sigma, St. Louis, MS). After 12 days of incubation, unreactive sugar was removed by extensive dialysis against PBS buffer. Control samples of each protein were also each incubated in PBS and protease inhibitors as above but without the addition of glucose.

Of the 23 hybridomas tested, five showed a differential recognition between nonenzymatically-glycated human plasma fibronectin and its normal counterpart based on a significant difference in the absorbance readings obtained. These data are summarized on Table IV, below.

TABLE IV
Differential Screening of Spent Medium from Hybridomas Against Human Plasma Fibronectin

| Hybridoma | $A_{490}$ of cFN | $A_{490}$ of gFN | % change from control |
|---|---|---|---|
| 10-C10 | 0.15 | 0.30 | 100.0 |
| 74-G11 | 0.12 | 0.22 | 83.3 |
| 75-F3 | 0.17 | 0.24 | 41.2 |
| 10-H9 | 0.23 | 0.31 | 34.8 |
| 74-D10 | 0.29 | 0.36 | 24.1 |

Spent media from several of the clones in Table I and II (10-H9, 26-B5, 74-D10, 74G-11, 83-D10, 84-C11 and 89-G4) were tested in the differential ELISA assay, described hereinabove, for the ability of antibodies from each cloned hybridoma to specifically recognize the nonenzymatically-glycated form of the major plasma proteins albumin, immunoglobulin G, and transferrin. Recognition was established when a significant increase in absorbance was observed in the ELISA assay when the spent medium from the clones was tested against nonenzymatically-glycated human plasma albumin, IgG, or transferrin over that which was found when medium was tested against the normal counterparts of these proteins.

MCA from one of the clones tsted, 83-D10, showed the ability to distinguish between the normal and nonenzymatically-glycated forms of these human proteins. Clone 83-D10 recognized nonenzymatically-glycated human albumin with an absorbance reading of 1.16 versus an absorbance reading of 0.60 for normal control human albumin (a 93.3% change in absorbance above the control level). Since albumin is the major component of human plasma, and its excretion into the urine of human diabetics is increased in diabetic renal disease, antibodies produced by clone 83-D10 may be useful in a diagnostic test for quantitating the levels of nonenzymatically-glycation of this readily-accessible protein in plasma, urine, other body fluids or in tissue samples.

Furthermore, clone 83-D10 also recognized the difference between normal and nonenzymatically-glycated human transferrin, another major plasma protein. Medium from this clone gave an absorbance reading of 1.11 for nonenzymatically-glycated transferrin versus an absorbance reading of 0.56 for control transferrin (a 98.2% change in absorbance above the control level). However, 83-D10 did not recognize the difference between nonenzymatically-glycated IgG and control IgG.

E. Discussion

In accord with the present method, murin hybridomas have been produced which secrete monoclonal antibodies which can bind to epitopes associated with nonenzymatically-glycated murine laminin (gLMN) and nonenzymatically-glycated murine total serum protein (gTSP). The hybridomas listed on Table I secrete MCAs which can distinguish gLMN from normal laminin (cLMN). The MCAs secreted by two of these hybridomas, 26-B5 and 10-C10 exhibit selective reactivity with serum proteins to the extent that they can distinguish between (a) plasma derived from two diabetic rats and (b) plasma derived from a normal rat (Table III). The MCA from 26-B5 apparently does not bind to nonenzymatically-glycated human fibronectin (gFN) while the antibody from 10-C10 strongly cross-reacts with gFN (Table IV). The antibody from 10-C10, as well as the antibody from hybridoma 74-G11 also exhibit differential recognition between gFN and normal fibronectin.

The hybridomas listed on Table II secrete MCAs which can distinguish nonenzymatically-glycated total murine serum protein (gTSP) from normal murine serum proteins (cTSP). For example, the MCAs secreted by hybridomas 83-D10 and 84-F9 are selective for gTSP over cTSP and also exhibit selective binding to serum proteins to the extent that they can readily distinguish normal rat plasma from plasma derived from a diabetic rat. Neither 83-D10 nor 84-F9 appear to cross-react with nonenzymatically-glycated human plasma fibronectin. However, the MCA excreted by 83-D10 was found to exhibit high selectivity with respect to its binding to the glycated and non-glycated forms of two major human plasma proteins, albumin and transferrin. Furthermore, as can be observed in the case of MCA 10-C10 and 83-D10, a given MCA which exhibits differential binding with respect to the glycated protein which was used as the immunogen can exhibit the same or an even higher reactivity with respect to a second unreduced, glycated protein.

Samples of hybridomas 26-B5 and 83-D10 have been deposited with the American Type Culture Collection, Rockville, MD, USA and have been assigned accession numbers HB9124 and HB9125, respectively.

A culture of the deposited microorganism will be made available to the public upon the grant of patent based upon the present application. It is to be understood that the availability of a deposit does not consititute a license to practice the subject invention in derogation of patent rights granted by the United States government.

Furthermore, the present invention is not to be limited in scope by the microorganism deposited, since the deposited hybridomas are intended as specific illustrations of discrete aspects of the invention. Indeed, various modifications of the invention in addition to those shown and described herein will become apparent to those skilled in the art from the foregoing description.

What is claimed is:

1. A hybridoma produced by a process comprising:
   (a) immunizing mammalian B lymphocytes with an effective amount of unreduced, nonenzymatically-glycated protein selected from the group consisting of total serum protein and laminin;
   (b) recovering the immunized B lymphocytes;
   (c) fusing said recovered B lymphocytes with malignant mammalian B lymphocytes to produce hybridomas;
   (d) selecting from said hybridomas a hybridoma which produces a monoclonal antibody which binds to an epitope on an unreduced, nonenzymatically-glycated protein, selected from the group consisting of total serum protein, fibronectin, transferrin and laminin, and which is substantially free of crossreactivity with the corresponding non-glycated protein when tested by enzyme-linked immunosorbent assay; and
   (e) clonally expanding said selected hybridomas.

2. The hybridoma of claim 1 wherein the immunized B lymphocytes are recovered from the spleens of an immunized mammal.

3. The hybridoma of claim 2 wherein the immunized mammal is a mouse.

4. The hybridoma of claim 2 wherein the B lymphocytes are fused with murine myeloma cells.

5. The hybridoma of claim 1 wherein the ammal is immunized with a murine protein.

6. The hybridoma of claim 1 wherein the mammal is immunized with an amount of unreduced, nonenzymatically-glycated total serum protein effective to immunize said mammal.

7. The hybridoma of claim 6 wherein the mammal is immunized with a murine protein.

8. A method of producing a population of hybridomas comprising:
(a) immunizing mammalian B lymphocytes with an effective amount of an unreduced, nonenzymatically-glycated protein selected from the group consisting of total serum protein and laminin;
(b) recovering the immunized B lymphocytes;
(c) fusing said recovered B lymphocytes with malignant mammalian B lymphocytes to produce hybridomas;
(d) selecting from said hybridomas a hybridoma which produces a monoclonal antibody which binds to an epitope on an unreduced, nonenzymatically-glycated plasma protein, and which is substantially free of cross-reactivity with the corresponding nonglycated plasma protein as tested by enzyme-linked immunosorbent assay;
(e) clonally expanding said selected hybridomas.

9. The method of claim 8 wherein the immunized B lymphocytes are recovered from the spleens of an immunized mammal.

10. The method of claim 8 wherein the immunized mammal is a mouse.

11. The method of claim 8 wherein the immunized B lymphocytes are fused with murine myeloma cells.

12. The method of claim 8 wherein the mammal is immunized with a murine protein.

13. The method of claim 8 wherein the mammal is immunized with an amount of unreduced, nonenzymatically-glycated total serum protein effective to immunize said mammal.

14. The method of claim 13 wherein the mammal is immunized with murine protein.

15. The method of claim 8 wherein the monoclonal antibody binds to an epitope on an unreduced, nonenzymatically-glycated human protein.

16. A monoclonal antibody which binds to an epitope on an unreduced, nonenzymatically-glycated protein selected from the group consisting of total serum protein, fibronectin, transferrin and laminin, wherein said glycated protein comprises glucose attached to an epsilon-amino group of a lysine residue in the polypeptide chain of the protein, and which antibody does not substantially cross-react with the corresponding nonglycated protein as tested by enzyme-linked immunosorbent assay.

17. The monoclonal antibody of claim 16 which is a murine monoclonal antibody.

18. The monoclonal antibody of claim 16 wherein the glycated protein is a human protein.

19. A method for detecting the presence of an unreduced, nonenzymatically-glycated protein in a tissue sample or a sample of a physiological fluid, which comprises reacting said sample with the monoclonal antibody of claims 1 or 16 and determining the presence of the protein-antibody complexes by reacting the complex with an antibody against said monoclonal antibody, wherein said antibody is bound to a detectable label.

20. The method of claim 19 wherein said fluid is blood.

21. The method of claim 19 wherein said fluid is urine.

22. The method of claim 19 wherein said fluid is saliva.

* * * * *

UNITED STATES PATENT AND TRADEMARK OFFICE
CERTIFICATE OF CORRECTION

PATENT NO. : 4,797,473

DATED : January 10, 1989

INVENTOR(S) : Joseph F. Tarsio and Leo T. Furcht

It is certified that error appears in the above-identified patent and that said Letters Patent is hereby corrected as shown below:

At Col. 3, line 51, for "MCAa" read --MCAs--.

At Col. 3, line 68, after "an" insert --unreduced, glycated protein versus the corresponding--.

At Col. 6, line 47, for "Pc/NSI/1-Ag 4.1" read --P3/NSI/1-Ag 4.1--.

At Col. 11, line 11, for "00" read --100--.

At Col. 12, line 57, for "theylenediamine" read --ethylenediamine--.

At Col. 15, line 5, for "ammal" read --mammal--.

Signed and Sealed this

Twenty-fourth Day of April, 1990

Attest:

HARRY F. MANBECK, JR.

*Attesting Officer*          *Commissioner of Patents and Trademarks*